United States Patent
Forster

Patent Number: 6,006,585
Date of Patent: *Dec. 28, 1999

[54] OPTOACOUSTIC GAS SENSOR

[75] Inventor: Martin Forster, Jona, Switzerland

[73] Assignee: Cerberus AG, Mannedorf, Switzerland

[ * ] Notice: This patent issued on a continued prosecution application filed under 37 CFR 1.53(d), and is subject to the twenty year patent term provisions of 35 U.S.C. 154(a)(2).

[21] Appl. No.: 09/010,657

[22] Filed: Jan. 22, 1998

[30] Foreign Application Priority Data

Jan. 25, 1997 [EP] European Pat. Off. ............. 97101168

[51] Int. Cl.[6] .............................. G01N 29/02; G01J 3/42; G01M 3/20
[52] U.S. Cl. .................... 73/24.01; 73/587; 73/24.02; 73/601; 250/343; 356/437; 422/83
[58] Field of Search ................. 73/24.01, 24.02, 73/587, 601; 250/344–3, 345, 343; 356/437, 438, 433; 422/83, 127

[56] References Cited

U.S. PATENT DOCUMENTS

| | | | |
|---|---|---|---|
| 3,385,100 | 5/1968 | Michael | 73/23.1 |
| 3,410,145 | 11/1968 | Daiber et al. | 73/432 |
| 3,417,606 | 12/1968 | Werner et al. | 73/24 |
| 4,019,056 | 4/1977 | Block et al. | 250/344 |
| 4,058,725 | 11/1977 | Aine | 250/343 |
| 4,067,653 | 1/1978 | Fletcher et al. | 356/204 |
| 4,110,686 | 8/1978 | Leskovar et al. | 324/58.5 C |
| 4,200,399 | 4/1980 | Kimble et al. | 356/437 |
| 4,234,258 | 11/1980 | Margolis et al. | 356/437 |
| 4,457,162 | 7/1984 | Rush et al. | 73/24 |
| 4,557,603 | 12/1985 | Oehler | 356/418 |
| 4,563,894 | 1/1986 | Karrer | 73/24 |
| 4,740,086 | 4/1988 | Oehler et al. | 356/432 |
| 5,178,836 | 1/1993 | Kitamori et al. | 422/73 |
| 5,540,079 | 7/1996 | Brown et al. | 73/23.33 |
| 5,616,826 | 4/1997 | Pellaux et al. | 73/24.02 |
| 5,753,797 | 5/1998 | Forster et al. | 73/24.01 |
| 5,780,724 | 7/1998 | Olender et al. | 73/40.5 A |

FOREIGN PATENT DOCUMENTS

| | | |
|---|---|---|
| 0760474 | 3/1997 | European Pat. Off. . |
| 0798552 | 10/1997 | European Pat. Off. . |
| 0801296 | 10/1997 | European Pat. Off. . |

*Primary Examiner*—Hezron Williams
*Assistant Examiner*—J. David Wiggins
*Attorney, Agent, or Firm*—Baker & Botts, LLP

[57] ABSTRACT

In an optoacoustic gas sensor having a sensor body (1, 2), a light source (10), a measurement cell (6) with a gas-permeable membrane (15), a measurement microphone (13), and an optical measurement filter (11) between the light source (10) and the measurement cell (6), a reference cell (7) is included that is separate from the measurement cell (6). The reference cell (7) has a reference microphone (14) that is shielded against optoacoustic signals from the gas to be detected via the reference cell being substantially free from intensity-modulated optical radiation having an absorption wavelength of the gas to be detected. The measurement signal, which indicates gas concentration, is obtained by subtraction of the signals from the two microphones (13, 14).

10 Claims, 1 Drawing Sheet

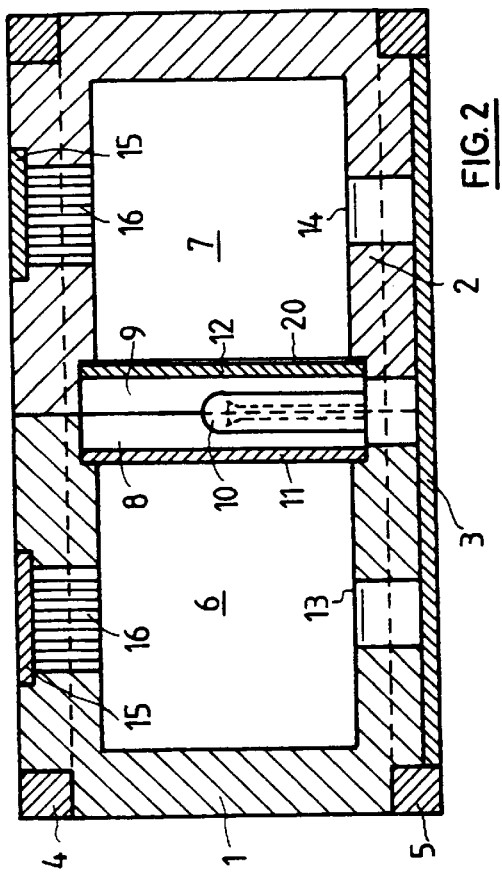
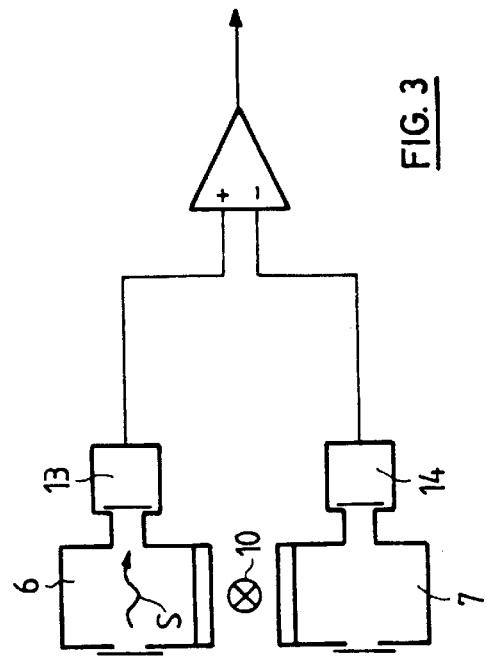
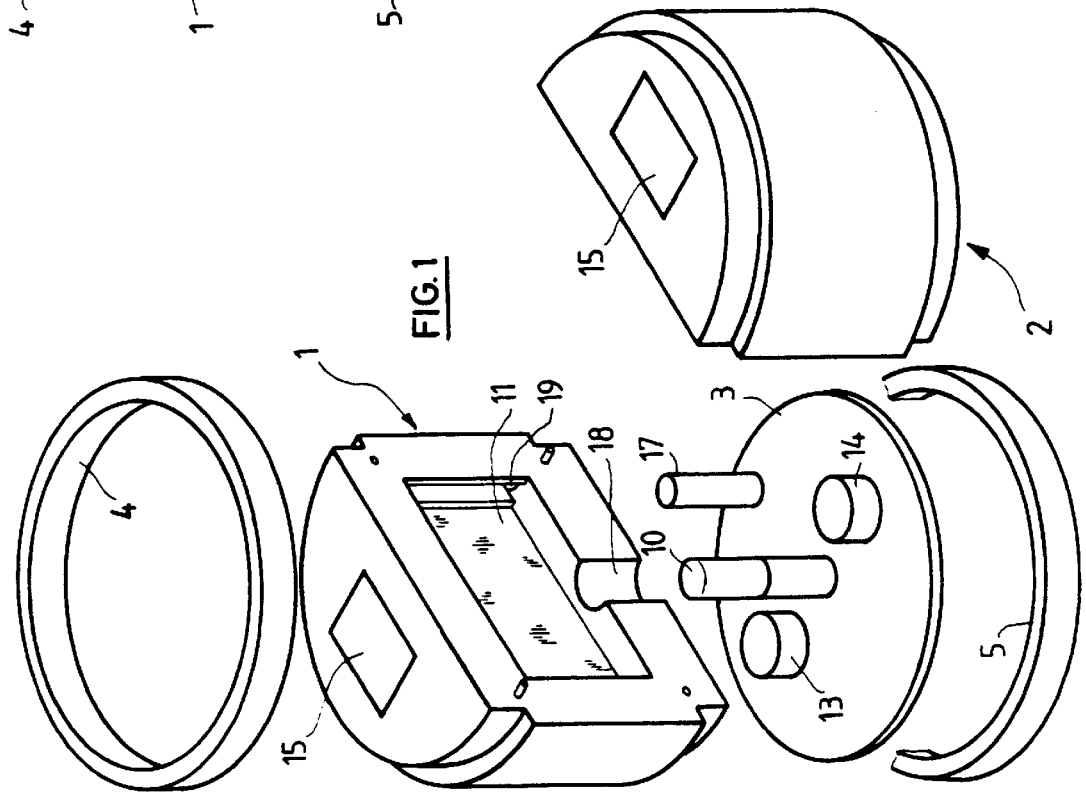

OPTOACOUSTIC GAS SENSOR

BACKGROUND OF THE INVENTION

The present invention relates to an optoacoustic gas sensor and, more particularly, to an optoacoustic gas sensor with a sensor body having a light source, a measurement cell with a gas-permeable membrane and a measurement microphone, and evaluation electronics.

Such gas sensors operate on the basis of the photoacoustic effect, whereby modulated-light irradiation of a gas to be detected gives rise to an acoustic pressure wave whose magnitude is directly related to the concentration of the gas. The acoustic pressure wave arises as the gas absorbs the optical radiation and heats up and expands as a result. The pressure fluctuations correspond to the modulation of the optical radiation.

From the measured acoustic pressure, the gas concentration can be inferred. Different gases are distinguished by use of light sources having different wavelengths corresponding to specific absorption wavelengths of the gases. Laser sources, or broadband light sources such as coiled filaments together with band-pass filters, can be used for this purpose. Gas sensors of this are described in European patent applications EP-A-0 760 474 and EP-A-0 798 552, and in respectively corresponding U.S. patent application Ser. No. 08/706,240 of Sep. 4, 1996 and Ser. No. 08/828,837 of Mar. 24, 1997 which are incorporated herein by reference.

Preferred gas sensors have a measurement cell whose longitudinal axis extends perpendicular to the longitudinal axis of the sensor body, and have a light source which is disposed to irradiate the measurement cell without irradiating the membrane, thus to minimize interference signals. Also, such gas sensors are explosion-proof, as the light source is sealed off from the ambient atmosphere. This type of photoacoustic sensor has proven effective in use, at least so long as the concentration of the gases to be detected lies above a certain minimum concentration, which for $CO_2$ is practically always the case. But combustible solvents containing CH bonds in the range from 300 to 3,000 ppm, or $NH_3$ in the range from 100 to 200 ppm are not readily detectable with such a sensor.

Potentially, the detection of combustible solvents containing CH bonds is a particularly important application for optoacoustic gas sensors, as pelliators can be used only to a limited extent in the range from 300 to 3,000 ppm, and can become contaminated easily. Metal-oxide sensors would be suitable, but they suffer from instability.

The sensitivity of optoacoustic gas sensors is limited due to interference signals caused by wall effects (zero signal), fluctuations in air pressure (caused by the actuation of doors or of ventilation systems), and vibrations (of the building or due to motors or persons). An immediate remedy for minimizing the effect of interference signals lies in the use of larger measurement cells and larger light sources. However, this would result in an appreciable increase in the dimensions of the sensor body and to a corresponding increase in sensor costs.

SUMMARY OF THE INVENTION

For enhanced sensitivity in an optoacoustic gas sensor of the type described above, including a measurement microphone in a measurement cell, the sensor body comprises a separate reference cell with a reference microphone that is shielded against optoacoustic signals from the gas to be measured, and with subtraction of the two microphone signals by the evaluation electronics. As a result of the subtraction, interference signals caused by vibrations or air pressure fluctuation are eliminated, the former through the use of the reference microphone which receives no optoacoustic signals from the gas to be measured, and the latter by virtue of the spatially separate reference cell with the reference microphone.

In a preferred embodiment of the invention, an optical reference filter is disposed between the light source and the reference cell, blocking direct radiation from the light source into the reference cell or transmitting only radiation which is not absorbed, or absorbed only insignificantly by the gas to be measured. The reference filter shields the reference cell against optoacoustic signals from the gas to be detected, thus preventing such signals from reaching the reference microphone. The reference filter also shields against zero signals caused by wall effects which originate primarily from the modulated heating of the optical filter which is disposed between the light source and the measurement cell.

In *Springer Series in Optical Sciences*, Vol. 62, *Photoacoustic and Photothermal Phenomena II*, p. 369, an optoacoustic sensor is described by O. Oehler and H. Blum, having two measurement cells, two light sources, two optical filters, and a symmetrical microphone disposed between the measurement cells, with a diaphragm which communicates with the gas volumes of the two measurement cells. Both measurement cells receive pulsed light having the same frequency, with the two light intensities being out of phase by 180°. The two cells are connected via valves to a test chamber containing a tree leaf whose gas activities are to be measured. The air in the system is recirculated by pumping, and measurements are taken between pump strokes.

The optoacoustic gas sensor described by Oehler et al., having two measurement cells and one microphone, is not suitable for present purposes because (i) mechanical vibrations transmitted to the diaphragm of the microphone cannot be compensated and hence give rise to interference signals, and (ii) zero signals caused by wall effects likewise cannot be compensated. Also, that gas sensor is rather difficult to manufacture, and costly.

BRIEF DESCRIPTION OF THE DRAWING

FIG. 1 an exploded representation of a gas sensor according to an exemplary embodiment the invention;

FIG. 2 a schematic axial section through the gas sensor of FIG. 1; and

FIG. 3 a block diagram of the gas sensor of FIG. 1.

DETAILED DESCRIPTION

As shown, the gas sensor consists of twin hemispherical casing halves 1 and 2 made of injection-molded aluminum or another suitable material and forming a cylindrical sensor body when joined, a printed circuit board 3, and two retaining rings 4 and 5. Each of the two casing halves 1 and 2 contains a cylindrical chamber, with the chamber of one casing half 1 serving as measurement cell 6 and the chamber of the other casing half 2 serving as reference cell 7. In the two casing halves 1 and 2, respective chambers 8 and 9 are disposed in front of the respective measurement cells 6 and 7, for accepting a light source 10 which is common to the measurement cell 6 and the reference cell 7. Each of the measurement cell 6 and the reference cell 7 is sealed off in the direction towards the light source 10, respectively by an optical measurement filter 11 and an optical reference filter 12. Preferably, the light source 10 is arranged so that its coiled filament is disposed on the extension of the longitudinal axes of the two cylindrical chambers, the measurement cell 6 and reference cell 7.

At their bottom surfaces, the measurement cell 6 and the reference cell 7 each comprises a bore for the passage of a measurement microphone 13 and a reference microphone 14, respectively. The upper front faces of the two casing halves 1 and 2 each comprise an opening that extends to the respective measurement cell 6 and the reference cell 7. Inserted into each of the openings are a gas-permeable membrane 15 and an adjoining perforated plate 16. The membrane 15, which is permeable to gas and impermeable to water droplets, consists of a fine-mesh material with pore size in the nanometer range. The perforated plates 16 support the membranes 15 and prevent direct irradiation of the membranes 15 by the light source 10. The measurement microphone 13, reference microphone 14 and light source 10 are mounted on the printed circuit board 3, which further bears a photodiode 17 for monitoring the intensity of the light emitted by the light source 10.

In the base of the chambers 8 and 9, bores 18 and 19 permit insertion of the light source 10 and the photodiode 17, with the bore 18 for the light source 10 being disposed at the interface between the two casing halves 1 and 2 so that half of the light source 10 is located in each of the casing halves 1 and 2. The bore 19 for the photodiode 17 can be disposed in the base of one chamber (8) as shown; alternatively, it may be disposed like the bore 18, with one half in each chamber. When the casing halves 1 and 2 are twins, having the same shape, the same casting mold can be used for manufacture, and the chamber 9 will have the same bores as chamber 8. Instead of a common light source 10 for the measurement cell 6 and the reference cell 7, each of the cells may have a separate light source.

On their planar lateral surfaces, the two casing halves 1 and 2 are provided with bolts an corresponding holes for guidance and adjustment. In an operation-ready state of the sensor, the measurement filter 11 and the reference filter 12 are secured with adhesive in the respective sensor halves I and 2, and the sensor halves 1 and 2 are fitted together at their planar lateral surfaces and fixed with the rings 4 and 5 and firmly connected, preferably bonded or glued together. The printed circuit board 3 is fastened to the sensor body by encapsulation. The measurement cell 6 and the reference cell 7 are duplicates of each other, and so are the measurement microphone 13 and the reference microphone 14.

The printed circuit board 3 is connected to an additional printed circuit board (not shown) which includes driver and evaluation electronics. The light source 10 is a conventional lamp with a coiled filament, or a laser source. The photodiode 17 consists of a silicon cell and a daylight filter. In the case of a coiled-filament light source 10, the photodiode 17 measures the light intensity in a wavelength range near 900 nm, preferably. The coiled filament emits light over a broad spectral range which extends into the infrared range, and, typically, a spectral line in the infrared range is used for gas detection. It may be assumed that a control measurement of the light intensity at 900 nm is sufficiently significant and reliable for monitoring the light intensity in the infrared range. If the light source 10 preferentially radiates in the far-infrared range, an infrared sensor can be used instead of the silicon photo diode 17.

The driver electronics causes the light source 10 to switch on and off in an operating cycle of 1:3, with one switching cycle lasting about $\frac{1}{10}$ second. As a rule, heating of the coiled filament when the light source 10 is switched on is more rapid than cooling at turn-off, with an operating cycle of 1:3 providing for sufficient cooling of the coiled filament after turn-off. The output signals of the measurement microphone 13 and of the reference microphone 14 are fed to the evaluation electronics where one of the two signals is subtracted from the other, and the result is amplified and converted by phase-sensitive rectification into a direct-current voltage signal (FIG. 3). The gas concentration value is obtained by comparing the signal with stored calibration values with which gas concentration values are associated.

The measurement filter 11 and the reference filter 12 serve as optical band-pass filters whose characteristic transmission band includes/excludes the narrow spectral band which is characteristic of the gas to be detected. For the detection of $CO_2$ this spectral band is located at around 4.25 $\mu$m, for the detection of $NH_3$ at around 10 $\mu$m. The filters 11 and 12 are secured in their respective casing halves 1 and 2 with an adhesive that absorbs visible light, with such absorption preventing the measurement cell 6 and the reference cell 7 from being illuminated with undesirable wavelengths. As a result of the absorption of the visible light, the adhesive and the filters 11 and 12 heat up, giving rise to an acoustic signal which can be used for operational monitoring of components such as the microphones 13 and 14, the light source 10, and the photo diode 17. Indeed, in case this signal disappears, at least one of these components is failing. Suitable control circuitry is understood without illustration.

In operation of the gas sensor, gas present in the measurement cell is irradiated by modulated light from the light source 10. The gas absorbs the optical radiation and heats up as a result. The gas expands thermally in correspondence with the modulation of the optical radiation, its pressure fluctuates periodically, with the strength of the resulting acoustic pressure wave being directly related to the concentration of the gas. The gas concentration is determined by measuring the acoustic pressure.

Dependence of the measurement signal on dimensions and other characteristics of the measurement cell, and determination of the calibration curve are described in further detail in the above-referenced European patent application EP-A-0 760 474 and U.S. patent application Ser. No. 08/706, 240.

Without a reference cell 7 and a microphone 14, interference signals are superimposed on the signal to be measured, thus lowering the detection limit of the sensor. The interference signals are caused primarily by wall effects, fluctuations in air pressure, and vibrations.

The interference signals caused by vibrations are eliminated by use, in parallel with the measurement microphone 13, of a like reference microphone 14 which receives no optoacoustic signals S (FIG. 3) from the gas to be detected, and by subtraction of the signals from the two microphones. Interference signals caused by air pressure fluctuations (from ventilation systems, or due to opening and closing of doors and windows, for example) are eliminated by use of a reference cell 7 in parallel with the measurement cell 6 having a reference microphone 14. As the same interference signal is included as a component in the signals from both the measurement cell and the reference cell, subtraction of the two signals results in cancellation of the interference component and results in a measurement signal without the interference component. For elimination of interference signals caused by vibrations, the reference microphone 14 in the reference cell 7 must not receive any optoacoustic signals S from the gas to be detected. This condition can be satisfied most readily if gas in the reference cell 7 is not irradiated with modulated light, or if radiation reaching the reference cell 7 is not absorbed or absorbed only minimally by the gas to be detected.

Due to wall effects, so-called zero signals are produced, due mainly to modulated heating of the measurement filter 11, such wall effects are eliminated by a reference filter 12 disposed in the reference cell 7, being irradiated by a like light source and likewise heating up in modulated fashion. Preferably, as shown in FIGS. 1 and 2, a common light source 10 is included for the measurement cell 6 and the reference cell 7, When using a reference filter 12, care is required to ensure that it does not transmit into the reference cell 7 any direct radiation from the common light source that would be absorbed by the gas to be detected. For a reference filter 12 of a material which is at least partially absorptive in the visible range of the spectrum (e.g. silicon, blackened polyethylene, and the like), this condition is satisfied if the reference filter is provided with a reflective coating 20 on its side facing the reference cell 7 (FIG. 2), so that the reference filter has the following properties:

(i) as a result of absorption of the visible portion of the radiation from the light source 10, the reference filter 12 is heated to approximately the same temperature as the measurement filter 11;

(ii) at the reflective coating 20, the non-absorbed infrared radiation is reflected into the measurement cell 6, so that the useful signal is increased;

(iii) no direct infrared radiation from the light source 10 reaches the reference cell 7.

When using a reference filter 12 without the reflective coating 20, infrared radiation may penetrate into the reference cell 7, so that care is required to ensure that the infrared radiation entering into the reference cell 7 either has a different wavelength from the infrared radiation entering into the measurement cell 6, or else is absorbed minimally by the gas to be detected.

In assembly of the gas sensor, the measurement filter 11 and the reference filter 12 are secured with adhesive in each respective casing half 1 and 2, and the printed circuit board 3 is provided with the required components such as light source 10, measurement microphone 13, reference microphone 14 and photodiode 17. The two casing halves 1 and 2 are then adhered together and secured by passing the rings 4 and 5 over them, Finally, the printed circuit board 3 is fastened to the sensor body by encapsulation.

I claim:

1. An optoacoustic gas sensor having a sensor body comprising:

a light source (10) for emitting intensity-modulated optical radiation including an absorption wavelength of a gas to be detected;

a measurement cell (6) in optical communication with the light source (10) and in atmospheric communication with an ambient atmosphere, and comprising a measurement microphone (13) disposed for generating a measurement signal which at least in part is due to optoacoustic pressure variations from the gas to be detected;

a reference cell (7) in atmospheric communication with the ambient atmosphere said reference cell being substantially free from intensity modulated optical radiation having an absorption wavelength of the gas to be detected and comprising a reference microphone (14) disposed of generating a reference signal which is substantially free of a signal component due to optoacoustic pressure variations from the gas to be detected; and evaluation electronics connected to the measurement microphone (13) and the reference microphone (14) for generating an output signal which represents the measurement signal minus the reference signal.

2. The gas sensor according to claim 1, further comprising an optical measurement filter (11) for substantially passing only optical radiation at the absorption wavelength of the gas to be detected.

3. The gas sensor according to claim 1, wherein the atmospheric communication of the measurement cell (6) and the reference cell (7) with the ambient atmosphere is via respective gas-permeable membranes (15, 16).

4. The gas sensor according to claim 1, wherein the reference cell is in optical communication with the light source (10), and wherein the reference cell further comprises an optical reference filter (12) which is substantially opaque at least to radiation at the absorption wavelength of the gas to be detected.

5. The gas sensor according to claim 4, wherein the reference filter (12) is transparent at a wavelength other than any wavelength at which the gas to be detected is absorptive.

6. The gas sensor according to claim 4, wherein the reference filter (12) consists of a material that is transparent to infrared radiation and at least partially absorptive at wavelengths of visible light, and wherein the reference filter (12) bears a reflective coating (20) on its side facing the reference cell (7).

7. The gas sensor according to claim 4, wherein the sensor body consists of twin casing halves (1, 2), one (1) of which contains the measurement cell (6) and the measurement filter (11), and the other (2) of which contains the reference cell (7) and the reference filter (12).

8. The gas sensor according to claim 7, wherein the light source (10) is disposed such that half of the light source (10) is disposed in each of the casing halves (1, 2).

9. The gas sensor according to claim 7, wherein the measurement filter (11) and the reference filter (12) each is secured in its respective casing half (1, 2) with an adhesive that absorbs visible light.

10. The gas sensor according to claim 7, wherein the reference cell (7) is in optical communication with a separate light source.

* * * * *